United States Patent [19]

Williams et al.

[11] Patent Number: 4,473,076

[45] Date of Patent: Sep. 25, 1984

[54] SURGICAL KNIFE

[75] Inventors: Rodger W. Williams, Brentwood, Tenn.; Dale W. Raymond, Clearwater, Fla.; Charles W. Atwood, Nashville, Tenn.

[73] Assignee: VXTRA Development Limited 700 Division, Nashville, Tenn.

[21] Appl. No.: 366,154

[22] Filed: Apr. 7, 1982

[51] Int. Cl.³ ............................................. A61B 17/04
[52] U.S. Cl. ...................................... 128/305; 30/320
[58] Field of Search .................. 128/305, 310; 30/320, 30/293, 368, 287

[56] References Cited

U.S. PATENT DOCUMENTS

| 1,195,169 | 8/1916 | Adcock | 128/305 |
| 2,473,968 | 6/1949 | Paton | 128/310 |
| 2,941,511 | 6/1960 | Cieremans | 120/42.03 |
| 3,945,117 | 3/1976 | Beaver | 30/287 |
| 3,967,377 | 7/1976 | Wells | 30/320 |
| 4,027,295 | 5/1977 | Lieberman | 128/305 |

OTHER PUBLICATIONS

"A Micrometer Knife", Albrecht, *Transactions AAOO*, Mar., Apr., 1972.

*Primary Examiner*—John D. Yasko
*Attorney, Agent, or Firm*—Holman & Stern

[57] ABSTRACT

A surgical knife includes a blade secured to the knife body and having a cutting edge projecting transversely beyond the body profile. A slotted ski member is movable axially relative to the cutting edge to selectively expose the cutting edge by means of plural thread segments which cooperate to convert rotary motion to said axially controlled axial motion. The position of the ski and blade beyond the body profile enhances visibility of the incision. In the preferred embodiment, the ski is part of a shaft which is threadedly received in a spindle, which, in turn, is threadedly received in the same sense within the knife body. The ski shaft is precluded from rotary motion relative to the knife body and its threads have a greater pitch than the body threads; consequently, axial displacement of the spindle in one direction produces axial displacement of the ski in the opposite direction. The blade and blade holder, which remain stationary relative to the body, may be disposable so that the ski and ski translating mechanism can be re-used as desired. Alternatively, the entire knife assembly may be disposable.

20 Claims, 13 Drawing Figures

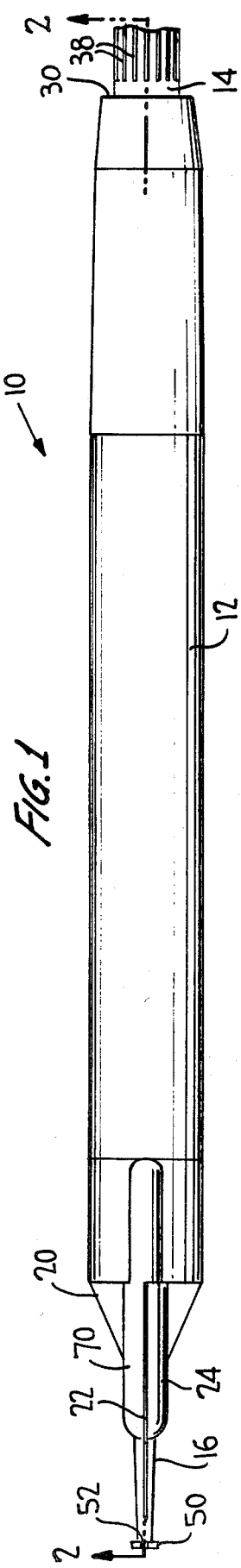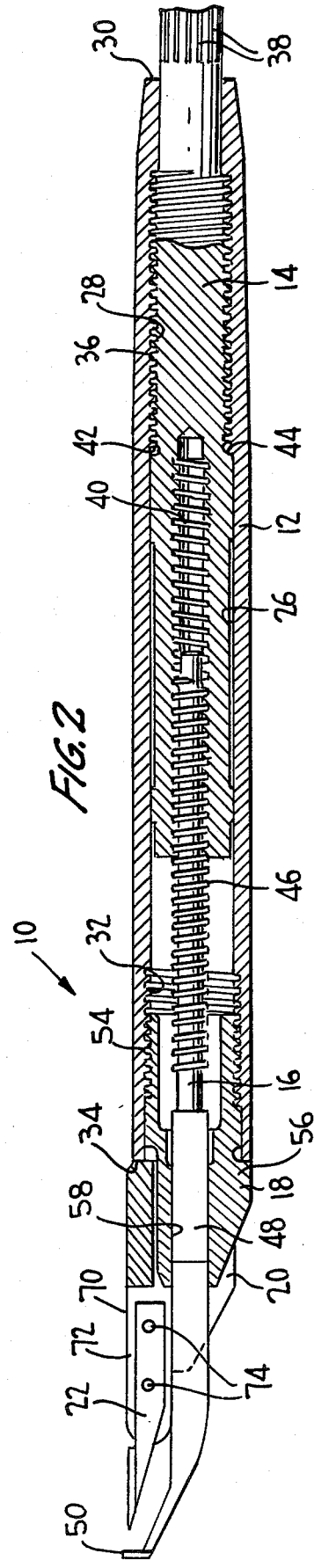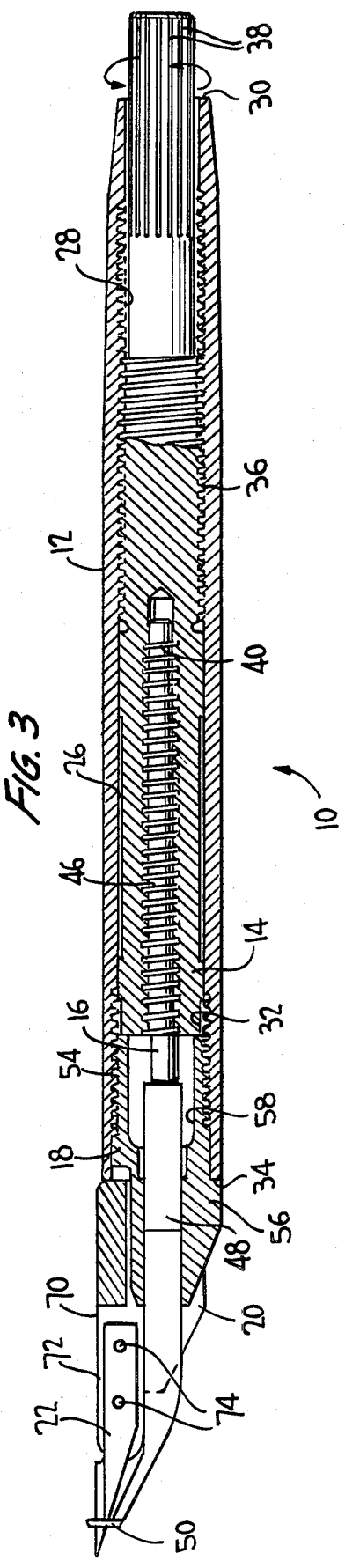

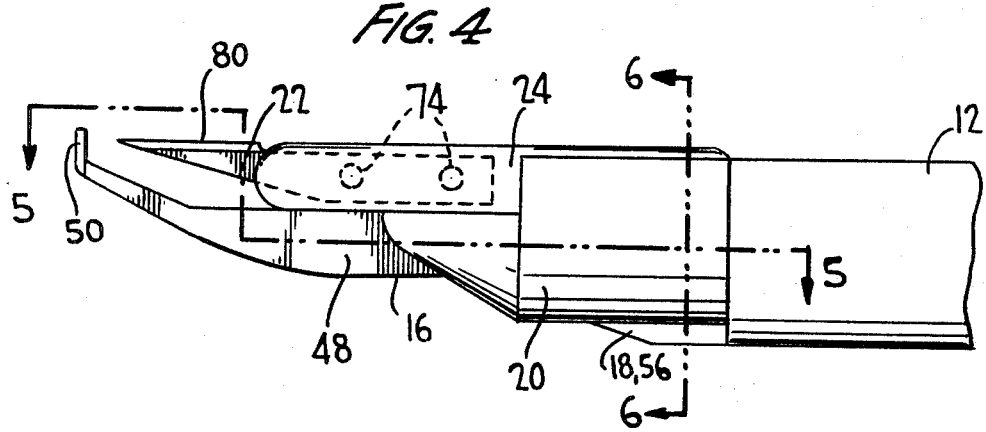
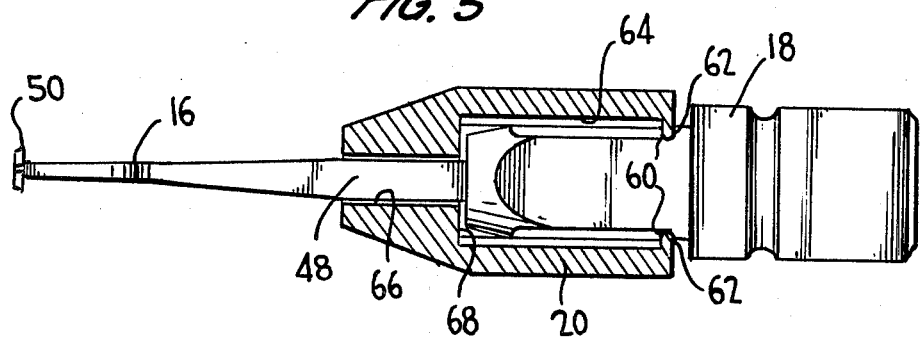
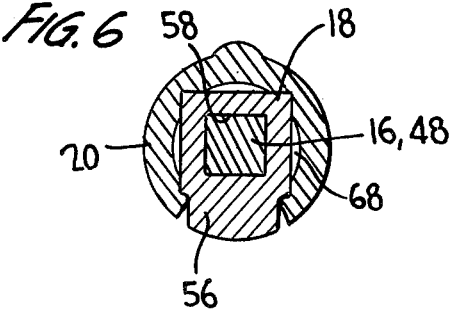

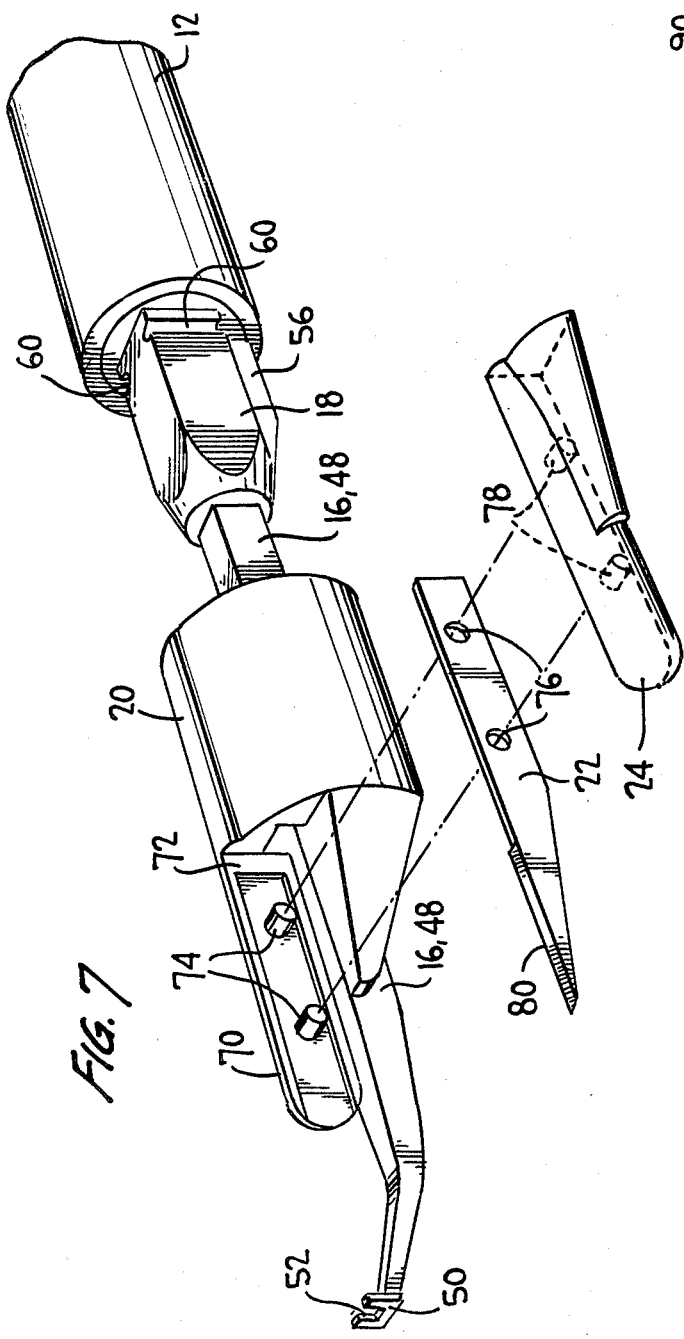
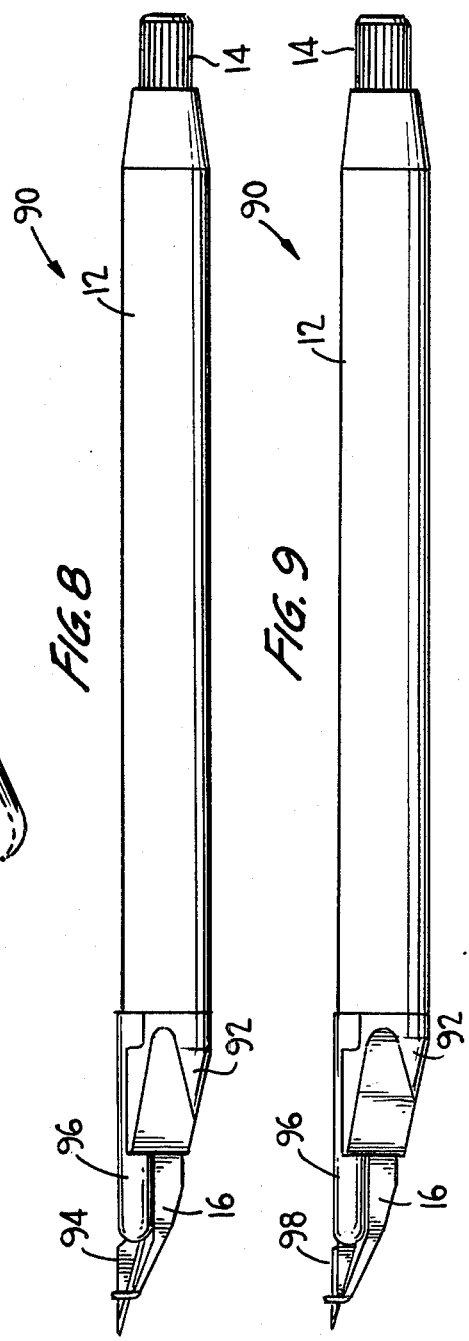

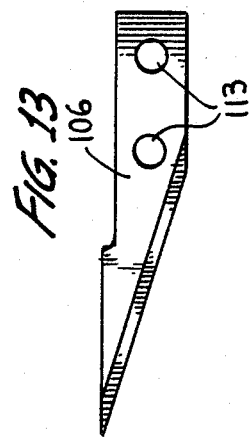
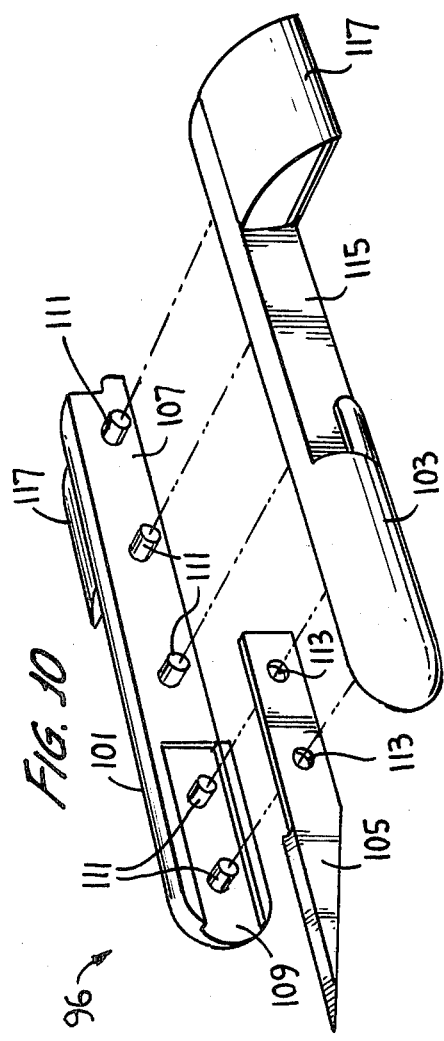
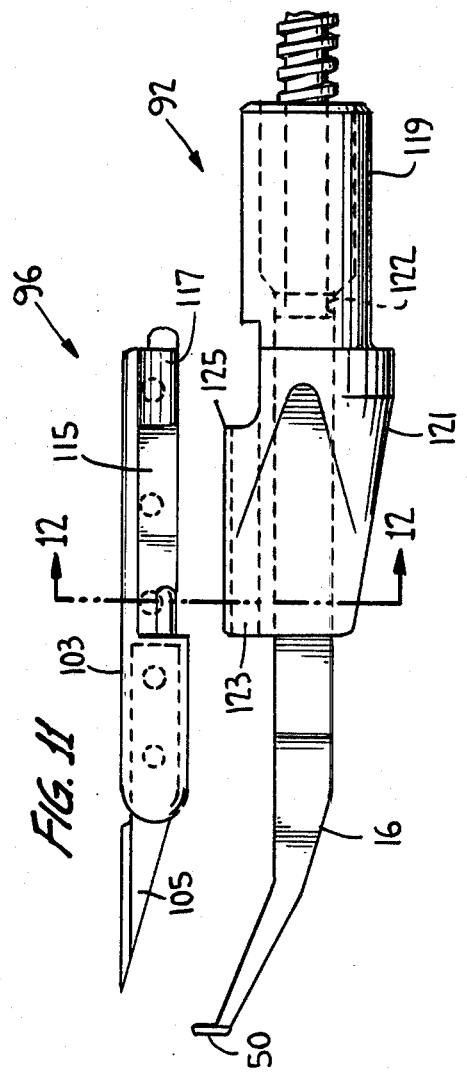
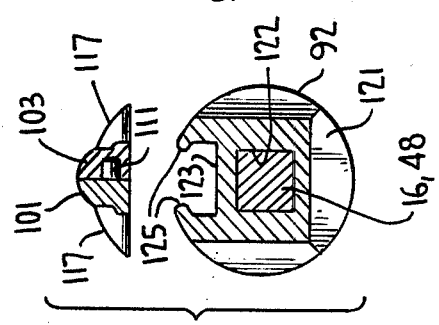

4,473,076

SURGICAL KNIFE

TECHNICAL FIELD

The present invention relates to surgical knives and, more particularly, to an improved surgical knife which permits accurate control of incision depth and improved visibility of the incision. The invention has primary utility in radial kerototomy surgery; however, it will be understood by those familiar with the art that the inventive concepts described herein apply to other types of surgery.

BACKGROUND OF THE INVENTION

In radial kerototomy surgery it is extremely important the percise depth of the incision be predeterminable. Specifically, a cut to depths deeper than intended may cause loss of eye fluid and permanent loss of sight. It is also desirable that different cuts be made to different depths, which depths must be accurately controlled to prevent the aforementioned undesirable effects of too deep an incision. Therefore, for radial kerototomy procedures, it is important to provide a surgical knife with a precisely controlled mechanism for exposing a predetermined blade depth. It is also important to assure that no more of the blade than the exposed predetermined depth be permitted to penetrate the eye. It is likewise important that such a knife arrangement be configured so that the incision, or a portion thereof, is not obscured by the knife body.

The prior art includes U.S. Pat. No. 3,967,377 to Wells, wherein a spindle is threadedly received in the knife body and, in turn, threadedly receives, in a common direction, a blade supporting chuck which is restrained from rotating relative to the body. The body thread pitch is greater than the chuck thread pitch so that, as the spindle is rotated into the body, the chuck retracts into the spindle by a lesser distance. The overall effect is a translation of the chuck by an amount proportional to the difference between the thread pitches. The arrangement provides precision control over blade movement; however, no adequate means is provided to preclude inadvertent insertion of the blade to a depth beyond the intended incision depth. Moreover, in the Wells device, movement of the blade back and forth relative to the body renders the blade subject to misalignment relative to the body member.

On the other hand, U.S. Pat. Nos. 4,026,295 to Lieberman and 3,945,117 to Beaver, disclose guards or ski members through which the blade projects and which rests against the eye surface to prevent inadvertent insertion of the blade to a depth greater than the exposed length of blade. However, the adjustment for blade length exposure in these devices is not very precise and the nature of the guard or ski structure precludes substantial improvement in this regard. Moreover, the bulky knife body requirements of these structures, and the bulky guard and ski structures, limit the surgeon's visibility of the incision without awkward positioning of the knife.

SUMMARY OF THE INVENTION

It is therefore an object of the present invention to provide an improved surgical knife wherein precise control over axial blade exposure is possible without sacrificing protection against too deep an incision.

It is another object of the present invention to provide an improved surgical knife in which the length of exposed blade portion is precisely controllable.

It is still another object of the present invention to provide a surgical knife wherein the exposed blade portion can be precisely varied without moving the blade in relation to the knife body.

It is still another object of the present invention to provide a surgical knife in which a ski member is provided to limit blade cutting depth but wherein precise control over blade exposure and optimum visibility of the incision is maintained.

In accordance with the present invention, a differentially threaded spindle arrangement is provided, similar to that of the Wells patent, but instead of translating the blade relative to the body, a ski shaft is translated relative to a stationary blade. The ski shaft has a slotted ski member at its distal end which extends transversely beyond the knife body profile. A knife blade is secured to the knife body with the cutting edge also extending beyond the body profile and in alignment with the ski slot. Axial translation of the ski which its shaft permits the ski to move over a range of positions which extend beyond the cutting edge of the blade. The use of the plural differential thread arrangement permits accurate control of the exposed blade length but does so by moving the ski or guard member rather than the blade itself. Projection of the ski slot and the knife beyond the body profile permits optimal vision of the incision by a surgeon.

BRIEF DESCRIPTION OF THE DRAWINGS

The above and still further objects, features, and advantages of the present invention will become apparent upon consideration of the following detailed description of a specific embodiment thereof, especially when taken in conjunction with the accompanying drawings, wherein:

FIG. 1 is a top view in plan of a knife in accordance with one embodiment of the present invention and wherein the ski member of the knife is fully extended;

FIG. 2 is a view in section taken along lines 2—2 of FIG. 1;

FIG. 3 is a view in section similar to FIG. 2 but showing the ski member of the knife fully retracted;

FIG. 4 is an enlarged side view in plan of the forward end of the knife of FIG. 1;

FIG. 5 is a view in section taken along lines 5—5 of FIG. 4;

FIG. 6 is a view in section taken along lines 6—6 of FIG. 4;

FIG. 7 is an exploded view in perspective of the forward end of the knife of FIG. 1;

FIG. 8 is a side view in plan of a knife in accordance with a second embodiment of the present invention wherein the blade is a ventral-type blade;

FIG. 9 is a side view in plan of the knife of FIG. 8 wherein the blade is a dorsal-type blade;

FIG. 10 is an exploded view in perspective of a blade cartridge employed in the embodiment of FIGS. 8 and 9;

FIG. 11 is an exploded side view in plan of the cartridge and nose portion of the knife embodiment of FIGS. 8 and 9;

FIG. 12 is a view in section taken along lines 12—12 of FIG. 11; and

FIG. 13 is a plan view of a ventral-type blade which can be substituted for the dorsal-type blade employed in FIG. 10.

DESCRIPTION OF THE PREFERRED EMBODIMENTS

Referring to FIGS. 1-7 of the drawings in greater detail, a surgical knife according to the present invention includes seven (7) basic parts, namely: an elongated body member 12; a spindle 14; a ski shaft 16; a nose member 18; a saddle member 20; a blade 22; and a blade clamp member 24. Body member 12 has a generally cylindrical profile and has a bore 26 defined therethrough along its entire length. Bore 26 has a cylindrical threaded portion 28 near its proximal end 30. A second threaded portion 32 of bore 26 is located near the distal end 34 of body member 12.

Spindle 14 is an elongated member having an externally threaded sector 36 which cooperatively engages with the bore 26. The proximal end of spindle 14 is provided with a series of angularly spaced longitudinally-extending grooves defining a handle which projects rearwardly from the proximal end 30 of body member 12. The distal end of spindle 14 has a threaded bore 40 defined therein and extending longitudinally rearward to the spindle. Threaded bore 40 constitutes a second threaded sector of the spindle 14. The overall length of spindle 14 is somewhat shorter than the length of body member 12 and the mutually engaged threaded bore portion 28 and threaded sector 36 are arranged so that at least a portion of the grooves 38 in the spindle handle are exposed at the proximal end 30 of body member 12.

An annular ledge 42 is defined in bore 26 at the end of threaded portion 28 remote from proximal end 30 of the body member 12. An enlarged radial portion 44 of spindle 14 cooperates with annular ledge 42 to limit axial displacement of spindle 14 in the direction of proximal end 30 of body member 12.

The ski shaft 16 has an externally threaded segment 46 extending from near its proximal end for a substantial distance along the ski shaft length. Proceeding in the direction of the distal end of ski shaft 14, a short cylindrical section of the ski shaft separates the threaded segment 46 from a coaxially disposed segment 48 of rectangular transverse cross-section. In the particular embodiment illustrated, segment 48 has a square cross-section. Segment 48 projects from the distal end 34 of body member 12 whereupon it tapers with a decreasing rectangular cross-section. The distal end of shaft 16 bends at an acute angle relative to the common longitudinal axis of shaft 16 until reaching its terminus which takes the form of a flat ski member 50 bent perpendicular to the longitudinal axis of the shaft and extending beyond the profile of body member 12. The radial or transverse extremity of ski member 50 is provided with a transversely or radially extending slot 52 which serves to bifurcate the ski member. The threaded segment 46 of the ski shaft cooperatively engages the threaded bore 40 of spindle 14. The threads of threaded bore section 28 of body member 12 and externally threaded sector 36 of the spindle are in the same direction as the threads in threaded bore section 40 of the spindle and externally threaded segment 46 of the ski shaft.

Nose member 18 has a cylindrical threaded portion 54 disposed at one end and arranged to cooperatively engage the second threaded portion 32 of body member 12. This threaded portion 54 of nose member 18 is received in bore 26 at the distal end 34 of body member 12. A radially enlarged portion 56 of nose member 18, which has a generally rectangular cross-section, serves as a stop against the distal end 34 of body member 12 to limit insertion of the nose member 18 into the body member. The rectangular cross-section of the nose member tapers in the distal direction. A bore 58 is defined longitudinally through nose member 18 and, throughout portion 56 has a cross-section which matches the cross-section of segment 48 of the ski shaft 16. Bore 58 thus serves as a guide member to permit longitudinal translation of shaft 16 therethrough but limiting rotation of shaft 16 relative to the nose member 18. Since the nose member 18 is secured to body member 12 by means of threaded portions 32 and 54, bore 58 also precludes rotation of shaft 16 relative to body member 12. Two (2) opposite sides of section 56 of the nose member are provided with opposed recesses 60 which define an imaginary plane that is perpendicular to the longitudinal axis of ski shaft 16. These recesses 60, which are best illustrated in FIGS. 5 and 7, cooperate with radially-inward extending lips 62 of saddle member 20 to maintain the saddle member fixed in position relative to nose member 18. Saddle member 20 is provided with a longitudinally-extending channel having two (2) sections 64 and 66 of different configuration. Specifically, channel section 64, as best seen in FIG. 6, fits over the top of the radially enlarged section 56 of nose member 18. Suitable cut-away portions of channel 64 are provided so as to engage the corners of the rectangular portion 56 and thereby preclude relative rotation between nose member 18 and the saddle member 20. One longitudinal end of channel section 64 is demarked by ribs 62 which, as noted above, engage the recesses 60 in nose member section 56 to prevent longitudinal displacement between the nose member 18 and saddle member 20. The other end of channel section 64 terminates in a generally U-shaped shoulder 68 which defines one end of channel section 66. This channel section is disposed about a portion of segment 48 of the ski shaft 16 which is slidable through channel section 66 as it moves longitudinally through bore 58 in nose member 18. The forward end of saddle member 20 has a forwardly projecting finger 70 with a substantially planar surface extending parallel to the longitudinal axis of saddle member 20 and body member 12. Two (2) longitudinally spaced transversely projecting cylindrical stubs extend from surface 74 and project through two (2) similarly spaced holes 76 defined transversely through blade 22. Blade clamp 24 has a flat surface which abuts the side of blade 22 opposite surface 72 of finger 70 and includes two (2) spaced bores 78 which receive stubs 74. The clamp 24 and saddle 20 are made of a plastic material which is heat-treatable such that stubs 74, when subjected to heat, form a bond with the blade clamp 24 in bores 78. The blade 22 is thus firmly held in place by the joined blade clamp 24 and projecting finger 70. The blade, when thusly held, is longitudinally aligned with slot 52 in ski member 50. The cutting edge of the blade projects transversely slightly beyond the profile of body member 12 so that the cutting edge can be readily viewed by the user of the device making an incision without undue manipulation of body member 12.

In operation, as spindle 14 is threaded into body member 12, ski shaft 16, which is prevented from rotating by nose member 18, is retracted into the spindle. If, as assumed in the present case, the pitch between threades of threaded bore 40 and externally threaded segment 46 is greater than the pitch between threads between threaded bore portion 28 and externally threaded segment 36, the net axial displacement of ski 50 is toward housing member 12. In other words, if spindle 14 is rotated one full turn relative to housing 12, the net axial displacement of the spindle with respect to the housing equals the pitch of the threads in sector 36 and bore portion 28. This, of itself, would tend to displace ski 50 to the left as viewed in FIG. 2. However, since ski shaft 16 is prevented from rotating, a one turn advancement of spindle 14 produces a one turn retraction of ski shaft 16 into the spindle. This superimposes a movement to the right, as viewed in FIG. 2, of the ski shaft 16 and ski 50. The net displacement of the ski member 50 is the thread pitch of sector 40 minus the thread pitch of sector 36. This differential thread relationship permits very fine and precise control of the axial displacement of ski shaft 50. Axial insertion of the spindle 14 into body member 12 is limited by the end of nose member 18 which abuts the end of spindle 14 when the spindle is fully inserted. The range of permissible axial displacement of spindle 14 within body member 12 is selected to permit ski member 50 to move between one extreme position, illustrated in FIG. 2, and another extreme position, generally illustrated in FIG. 3. Specifically, the position of the ski member 50 in FIG. 2 is such that the ski member projects beyond the distal extremity of blade 22 so that no portion of the blade extends beyond the ski member. In FIG. 3, the blade is illustrated as projecting through the slot in ski member 50 to expose some predetermined maximum length of the blade beyond the ski member. The amount of blade projection beyond the ski member can be adjusted by appropriately positioning spindle 14 in body member 12. Importantly, however, is the fact that the blade member does not move; rather, it is the ski member 50 that is translated longitudinally to expose more or less of the blade through slot 52.

Since the blade clamp assembly 24 and blade 22, along with saddle member 20, may be readily removed from the assembly by forcing ribs 62 out of engagement with recesses 60 and sliding the the saddle member 20 over the ski shaft and ski member 50. In this sense, the saddle, blade clamp and blade are disposable, and can be replaced after use.

The degree of control of translation of ski member 50 is, of course, dependent upon the difference between the pitches in threaded sectors 36 and 40 of the spindle. By way of example only, in one embodiment, the pitch of the threads in sector 40 and segment 46 is 1/28 inch or 0.0357 inch. The corresponding pitch in externally threaded sector 36 and threaded bore portion 28 is 1/36 inch or 0.0278 inch. The net axial displacement of ski member 50 in response to one full turn of spindle 14, therefore, is 0.0357-0.0278 or 0.0079 inches. In this exemplary embodiment, the full range of axial displacement of ski member 50 is 0.125 inches. The blade member 22 for such an embodiment is typically ⅜ inch with a length of cutting edge 80 equal to approximately 0.233 inch.

A second embodiment 90 of the knife of the present invention is illustrated in FIGS. 8–13 wherein identical parts for those illustrated in FIGS. 1–7 bear the same reference numerals. Referring specifically to FIG. 8, knife 90 includes an elongated body member 12, a spindle 14, a ski shaft 16, a nose member 92, a ventral-type blade 94, and a blade cartridge assembly 96. The identical structure appears in FIG. 9 also except that a dorsal-type blade 98 replaces the ventral-type blade 94 of FIG. 8. Knife 90 differs from knife 10 primarily by the elimination of saddle member 20 and the corresponding change in the structure of nose member 92 and the replacement of the blade clamp member 24 by the cartridge assembly 96. The interengagement of body member 12, spindle 14, and ski shaft 16 is identical to that described hereinabove in relation to knife 10 of FIGS. 1–7; therefore, this engagement will not be described in relation to knife 90.

Referring specifically to FIG. 10, the blade cartridge assembly 96 includes a pair of elongated members 101 and 103 which are generally semicylindrical with rounded front ends and which are adapted to fit together with a knife blade 105 therebetween. Member 101 has a surface 107 which, when the cartridge is assembled, mates with a similar surface of member 103. Surface 107 has a generally elongated recess 109 extending from its forward end in a rearward direction longitudinally of member 101. A similar recess (not visible in FIG. 10) is defined in the mating surface of member 103 so as to be aligned with recess 109. These recesses have a combined depth which is substantially equal to the thickness of knife blade 105 which resides within the two (2) recesses when members 101 and 103 are placed together. A plurality of stubs 111 extend perpendicularly from surface 107 and are longitudinally spaced along that surface. Member 103, on its mating surface, is provided with a plurality of bore (not illustrated), each of which is adapted to receive a respective stub 111 when members 101 and 103 are placed together. Two (2) of the stubs 111 extend from member 101 in the region of recess 109. Suitable holes 113 are provided in the knife blade 105 so that these stubs may project through holes 113 into the appropriate bores in member 103.

Each of members 101 and 103 include an intermediate longitudinal portion 115 of reduced thickness. Rearwardly of these portions 115 there is provided a radially extending wing-like member 117 which has a flat bottom surface and an arcuate top surface which converges toward the bottom surface to meet that surface in a straight edge.

Referring now to FIGS. 11 and 12, the nose member 92 includes a generally cylindrical rearward section 119 which is hollow to permit the threaded shaft of ski member 16 to pass therethrough. A forward portion 121 of the nose member is also hollow for this purpose and is provided with a longitudinally extending slot along its top side for receiving the recessed portion 115 of the assembled blade cartridge 96. Slot 123 is configured such that when the cartridge 96 is placed therein, blade member 105 projects forwardly and in alignment with the slot 52 in ski member 50 of the ski shaft 16. The longitudinally-extending upper edges 125 of slot 123 are bent inwardly so that the cartridge 96 can be snapped into slot 123 and engaged therein by the converging lips 125. The snap-fit of the cartridge in channel 123 thus holds the two (2) members 101 and 103 together with the knife blade 105 therebetween. This eliminates the need for a special step to assemble cartridge members 101 and 103 during the assembly of the overall knife unit.

Referring to FIG. 13, a ventral-type blade 106 is illustrated with suitable through holes 113 defined therein for mating with stubs 111. The ventral-type knife blade 106 can readily be substituted for the dorsal-type knife blade 105 illustrated in FIG. 1 so that the overall knife assembly can be fabricated irrespective of the blade type.

As can be seen from FIGS. 8 and 9, the rearward portion 119 of the nose member is inserted in the forward end of body member 12 when the unit is finally assembled so that the ski shaft 16 projects forwardly from the body member 12, through the nose member 92 and forwardly of cartridge 96. The threaded engagement between the ski shaft and spindle 14, and the threaded engagement between the spindle 14 and body member 12 remain the same as described above in relation to FIGS. 1–7. All of the parts of the embodiments of FIGS. 8–13, except for the knife blades 94, 98, 105, and 106 may be made of injection molded plastic. These parts, as described above, are easily and quickly assembled so that a minimum of manufacturing time and expense is involved. Therefore, the entire keratotomy knife assembly 90 is disposable after a single use.

As best seen in FIG. 12, the bore 122 which extends longitudinally through the forward section 121 of nose member 92 has a cross-section which matches the periphery 48 of the ski shaft 16 passing through this part of the nose member. Specifically, bore 122 has a square cross-section so as to serve as a guide to permit longitudinal translation of the ski shaft 16 therethrough; however, ski shaft 16 is prevented from rotating relative to the nose member by virtue of this bore configuration. Since, as described above, the rearward section 119 of nose member 92 is force-fitted into the forward end of body member 12, both the nose member and the ski shaft are prevented from rotating relative to the body member. Thus, by rotating spindle 14 relative to the body member, the ski shaft 16, in the manner described above in relation to FIGS. 1–3, is caused to slide longitudinally relative to the knife blade to thereby selectively expose more or less of the blade as desired. The position of the knife blade relative to the profile of the body member is substantially the same as described above in relation to the embodiments of FIGS. 1–7.

The surgical knife described herein is an improvement over the prior art by virtue of the fact that the ski member is translatable longitudinally rather than the blade member and that the bifurcated ski member 50 and cutting edge 80 extend transversely beyond the profile of body member 12. In addition, the unit is inexpensive and entirely disposable, thereby rendering the relatively more expensive extension and retraction mechanism reusable.

While we have described and illustrated a specific embodiment of our invention, it will be clear that variations of the details of construction which are specifically illustrated and described, may be resorted to without departing from the true spirit and scope of the invention as defined in the appended claims.

We claim:

1. A surgical knife comprising:
an elongated body member having a predetermined profile, first and second ends and a bore extending longitudinally therethrough, said bore having a cylindrical threaded portion;
spindle means having a first cylindrical externally threaded sector and a second threaded sector, said first threaded sector being arranged for cooperative engagement with said threaded portion of said body member;
shaft means having a longitudinal axis and one end which is bent to extend transversely of the longitudinal axis, said shaft means further including a cylindrically threaded segment for cooperatively engaging said second threaded sector of said spindle means, the threads of said segment and said second sector being of different pitch but common direction relative to the threads of said body member and said first sector, respectively;
means retaining said shaft means in said elongated body member with said one end of said shaft means projecting from a first end of said body member, said retaining means including guide means for preventing rotation of said shaft means relative to said body member while permitting axial motion of said shaft means relative to said body member; and
blade means secured to said body member and including a cutting edge extending axially beyond said first end of said body member;
wherein said one end of said shaft means is bifurcated by a slot longitudinally aligned with said cutting edge, whereby application of relatively large rotary motion to said spindle means results in relatively small axial motion of said one of said shaft means over a range of motion which permits said cutting edge to be selectively projected through said slot.

2. The surgical knife according to claim 1:
wherein said shaft means includes an intermediate segment positioned axially between one end and said threaded segment, said intermediate segment having a transverse cross-section with a periphery in the shape of a polygon; and
wherein said guide means includes a longitudinal bore extending therethrough having a transverse cross-section throughout at least part of its length which is polygonal to match the polygonal periphery of the cross-section of said intermediate segment of said shaft means.

3. The surgical knife according to claim 1, wherein said blade means is secured to said body member such that the cutting edge is disposed at a location beyond the axial projection of said predetermined profile of said body member, and wherein said one end of said shaft means likewise extends transversely beyond said predetermined profile.

4. The surgical knife according to claims 1 or 3, wherein said spindle means projects axially from said second end of said body member and includes a grip to facilitate manual rotation of said spindle means relative to said body member.

5. The surgical knife according to claims 1 or 3, wherein said blade means includes:
a disposable blade holder secured to the outer periphery of said body member approximate said first end; and
a blade including said cutting edge, held by said blade holder with said cutting edge disposed transversely beyond the predetermined profile of said body member.

6. The surgical knife according to claim 3:
wherein said shaft means includes an intermediate segment positioned axially between said one end and said threaded segment, said intermediate segment has a transverse cross-section with a periphery in the shape of a rectangle; and
wherein said guide means includes a longitudinal bore extending therethrough having a transverse cross-section throughout at least part of its length which is rectangular to match the rectangular periphery of the cross-section of said intermediate segment of said shaft means.

7. The surgical knife according to claims 1 or 3, wherein said body member and said spindle means have longitudinal axes disposed coaxially with the longitudinal axis of said shaft means.

8. The surgical knife according to claims 1 or 3, wherein the pitch of the threads of said segment and said second sector is greater than the pitch of the threads of said body member and said first sector.

9. The surgical knife according to claim 1, wherein said blade means is a dorsal-type blade.

10. The surgical knife according to claim 1, wherein said blade means is a ventral-type blade.

11. The surgical knife according to claim 1, wherein said body member, said spindle means, said shaft means, and said retaining means are made of injection molded plastic and wherein the entire surgical knife is disposable after a single use.

12. A surgical knife comprising:
an elongated body member having first and second ends and a predetermined profile;
blade means including a cutting edge immovably secured to said elongated body member such that said cutting edge permanently projects longitudinally beyond said first end and transversely beyond said predetermined profile;
ski means secured in said elongated body member and projecting beyond said first end, said ski means including a slotted portion extending transversely beyond said predetermined profile with a slot disposed in longitudinal alignment with said cutting edge; and
control means for selectively effecting mutual longitudinal displacement of said ski means and said blade means to permit selective longitudinal projection of said cutting edge through said slot.

13. The surgical knife according to claim 12, wherein said control means comprises:
a bore extending longitudinally through said body member and having a threaded portion;
spindle means having a first cylindrical externally threaded sector and a second threaded sector, said first threaded sector being arranged for cooperative engagement with said threaded portion of said body member;
shaft means having a cylindrical threaded segment for cooperatively engaging said second threaded sector of said spindle means, the threads of said segment and said second sector being of different pitch but common direction relative to the threads of said body member and said first sector, respectively;
wherein said ski means is secured to and movable with said shaft means; and
means retaining said shaft means in said elongated body member with said one end of said shaft means projecting from said first end of said body member, said retaining means including guide means for preventing rotation of said shaft means relative to said body member while permitting axial movement of said shaft means relative to said body member.

14. The surgical knife according to claim 13, wherein the pitch of the threads of said segment and said second sector is greater than the pitch of said threads of said body member and said first sector.

15. The surgical knife according to claims 12, 13, or 14:
wherein said shaft means includes an intermediate segment positioned axially between one end and said threaded segment, said intermediate segment having a transverse cross-section with a periphery in the shape of a polygon; and
wherein said guide means includes a longitudinal bore extending therethrough having a transverse cross-section throughout at least part of its length which is polygonal to match the polygonal periphery of the cross-section of said intermediate segment of said shaft means.

16. A surgical knife comprising:
an elongated body member having first and second ends and a predetermined profile;
blade means including a cutting edge immovably secured to said elongated body member such that said cutting edge permanently projects longitudinally beyond said first end;
ski means secured in said elongated body member and projecting beyond said first end, said ski means including a slot disposed in longitudinal alignment with said cutting edge;
blade deployment means for selectively effecting longitudinal displacement of said ski means relative to said body member and said blade means to permit selective longitudinal projection of said cutting edge through said slot.

17. The surgical knife according to claim 16 wherein said cutting edge projects transversely beyond said predetermined profile.

18. The surgical knife according to claim 16 wherein said blade deployment means comprises:
a bore extending longitudinally through said body member and having a threaded portion;
spindle means having a first cylindrically externally threaded sector and a second threaded sector, said first threaded sector being arranged for cooperative engagement with said threaded portion of said body member;
shaft means having a cylindrical threaded segment for cooperatively engaging said second threaded sector of said spindle means, the threads of said segment and said second sector being of different pitch but common direction relative to the threads of said body member and said first sector, respectively;
wherein said ski means is secured to and movable with said shaft means;
means retaining said shaft means in said elongated body member with said one end of said shaft means projecting from said first end of said body member, said retaining means including guide means for preventing rotation of said shaft means relative to said body member while permitting axial movement of said shaft means relative to said body member.

19. The surgical knife according to claim 18 wherein the pitch of the threads of said segment and said second sector is greater than the pitch of said threads of said body member and said first sector.

20. The surgical knife according to claim 18, wherein said shaft means includes an intermediate segment positioned axially between one end and said threaded segment, said intermediate segment having a transverse cross-section with a periphery in the shape of a polygon; and wherein said guide means includes a longitudinal bore extending therethrough having a transverse cross-section throughout at least a part of its length which is polygonal to match the polygonal periphery of the cross-section of said intermediate section of said shaft means.

* * * * *